US006632663B1

(12) United States Patent
Brunham

(10) Patent No.: US 6,632,663 B1
(45) Date of Patent: Oct. 14, 2003

(54) DNA IMMUNIZATION AGAINST CHLAMYDIA INFECTION

(75) Inventor: Robert C. Brunham, Winnipeg (CA)

(73) Assignee: Aventis Pasteur Limited, Toronto (CA)

( * ) Notice: Subject to any disclaimer, the term of this patent is extended or adjusted under 35 U.S.C. 154(b) by 0 days.

(21) Appl. No.: 09/401,780

(22) Filed: Sep. 22, 1999

(51) Int. Cl.$^7$ ............................................. C12N 15/63
(52) U.S. Cl. .................................................. 435/320.1
(58) Field of Search ........................... 435/320.1, 252.1; 536/23.1, 24.1; 424/93.21; 514/44

(56) References Cited

U.S. PATENT DOCUMENTS 5,589,466 A    12/1996  Felgner et al. ................. 514/44
6,001,372 A *  12/1999  DeMars et al. ............. 424/263.1

FOREIGN PATENT DOCUMENTS

EP           0192033       8/1986
WO         WO 98/02546 A   1/1998

OTHER PUBLICATIONS

Crystal, R. G. Transfer of genes to humans: early lessons and obstacles to success. Science. vol. 270, pp. 404–410, 1995.*
Leitner et al. DNA and RNA–based vaccines: principles, progress and prospects. Vaccine. vol. 18, pp. 765–777, 2000.*
Zhang et al. DNA vaccination with the major outer–membrane protein gene induces acquired immunity to *Chlamydia trachomatis* mouse pneumonitis infection. The Journal of Infectious Diseases. vol. 176. pp. 1035–1040. 1997.*
Chattergoon et al. Genetic immunization: a new era in vaccines and immune therapeutics. FASEB J. vol. 11, pp. 753–763. 1997.*
R.S. Stephens, Genembl Accession No. AE001337, Dec. 1999.*
T.D. Read, Nucleic Acids Research, "Genome sequences of *Chlamydia trachomatis* MoPn and *Chlamydia pneumoniae* AR39,"2000, vol. 28, No. 6,pp. 1397–1406.*
Donnelly et al, Ann. N.Y. Acad. Sci. 772 (1995) pp. 40–46.
D. M. Pardoll and A. M. Beckerieg, Immunity 3, 165–169 (1995).
W.M. McDonnell and F. K. Askari, N. Engl. J. Med. 334, 42–45 (1996).
J. B. Ulmer et al., Science 259, 1745–1749 (1993).
B. Wang et al., Proc. Natl. Acad.. Sci. USA 90,4156–4160 (1993).
G. J. M. Cox, T.J. Zamb, L.A. Babiuk, J. Virol. 67, 5664–5667(1993).
E. Raz et al., Proc. Natl.Acad. Sci. USA, 91,9519–9523(1994).
Z. Q. Xiang et al., Virology 199, 132–140 (1994).
J.J.Donnelly et al., J. Infect. Dis. 713, 314–320 (1996).
D. L. Montgomery et al., DNA. Cell. Biol. 12, 777–783 (1993).

J.J. Donnelly et al., Nature Medicine 1, 583–587 (1995).
G. H. Rhodes et al., Dev. Biol.Stand. 82, 229–236 (1994).
H. L. Davis, M. L Michel, R. G. Whalen, Human Molecular Genetics 2, 1847–1851 (1993).
J. B. Ulmer et al., Vaccine 12, 154 1–1544 (1994).
Z. Xiang and H. C. J. Ertl.immunity 2, 129–135 (1995).
E. F. Fynan et al, Proc. Natl. Acad. Sci. USA 90, 11478–11482 (1993).
E. Manickan, R. J. D. Rouse, Z. Yu, J. Immunol. 155, 259–265 (1995).
M. Sedegah et al , Proc. Natl.Acad. Sci., USA 91, 9866 (1994).
M.A. Barry, W.C. Lai, S.A. Johnston, Nature 377, 632–635 (1995).
D. Xu and F. Y. Liew, Vaccine 12, 1534–1536 (1994).
D. B. Lowrie, R.E. Tascon, M. J. Colston, Vaccine 12, 1537–1540 (1994).
J. W. Moulder, Microbiol. Rev. 55, 143–190 (1991).
J. Schachter, Curr. Top. Microbiol. Immunol, 138, 109–139 (1988).
S. D. Hillis and J. N. Wasserheit,N. Engl. J. Med. 334, 1399–1401 (1996).
R. C. Brunham and R. W. Peeling, Infectious Agents and Disease 3, 218–233 (1994).
R. P. Morrison, D.S. Manning, H. D. Caldwell, in Advances in Host Defence Mechanisms, T.C. Quinn, Ed. (Raven Press, New York, 1992), pp 57–84.
J. T. Grayston and S–P. Wang, Sex Trans. Dis. 5, 73–77 (1978).
J.T. Grayston and S.–P Wang, J. Infect.Dis. 132, 87–105 (1975).
H. R. Taylor, J. Whittum–Hudson, J. Schachter, Invest. Ophthalmol. Vis. Sci. 29, 1847–1853 (1988).
B.E. Batteiger, R. G. Rank, P.M. Bavoil, J. Gen. Microbiol. 139, 2965–2972 (1993).
M. Campos et al.,Invest. Ophthalmol. Vis. Sci. 36, 1477–1491 (1995).
H. Su, M. Parne, H. D. Caldwell, Vaccine 13, 1023–1032 (1995).
T.–W. Tan, A.J. Herring, I. E. Anderson, Infect. Immun. 58, 3101–3108 (1990).

(List continued on next page.)

*Primary Examiner*—Ram R. Shukla
(74) *Attorney, Agent, or Firm*—Sim & McBurney

(57) ABSTRACT

Nucleic acid, including DNA, immunization is used to generate a protective immune response in a host, including humans, to a serine-threonine kinase (STK) of a strain of Chlamydia. A non-replicating vector, including a plasmid vector, contains a nucleotide sequence encoding a STK or a fragment of the STK that generates antibodies that specifically react with STK and a promoter sequence operatively coupled co the first nucleotide sequence for expression of the STK in the host. The non-replicating vector may be formulated with a pharmaceutically-acceptable carrier for in vivo administration to the host.

1 Claim, 4 Drawing Sheets

OTHER PUBLICATIONS

M. Tuffrey, F. Alexander, W. Conlan, J. Gen. Microbiol. 138, 1707–1715 (1992).

Y.–X. Zhang, J. G. Fox, Y. Ho, Mol. Biol. Evol. 10, 1327–1342 (1993).

R. P. Morrison, K. Feilzer, D. B. Tumas, Infect. Immun. 63, 4661–4668 (1995).

H. Su and H. D. Caldwell, Infect. Immun. 63, 3302–3308 (1995).

J. U. Igietseme et al., Reg.Immunol. 5, 317–324 (1993).

J. U. Igietseme and R. G. Rank, Infect. Immun. 59, 1346–1351 (1991).

D. M. Williams, J. Schachter, J.J. Coalson, J. Infect. Dis. 149, 630–639 (1984).

G. Tipples and G. McClarty, J. Biol. Chem. 270, 7908–7914 (1995).

X. Yang, K. T. HayGlass, R. C. Brunham, J. Immunol., 156, 4338–4344 (1996).

Tang et al., Nature 1992, 356: 152–154.

Davis et al., Vaccine 1994, 12: 1503–1509.

Donnely et al: "Protective efficacy of intramuscular immunization with naked DNA" Annals New York Academy Of Sciences, vol. 772, 1995, pp. 40–46.

Lopez–Macia et al: "Induction of Antibodies against *Salmonella typhi* OmpC Porin by named DNA Immunization" Annals Of The New York Academy Of Sciences, vol. 772, 1995, pp. 285–288.

Green et al, "Liposomal Vaccines", Adv. Exp. Med. Biol. 383:83–92.

Baxby et al, "Potential use of nonreplicating vectors as recombinant vaccines", Vaccine, 10(1): 8–9.

Anderson et al, Immune response in mice following immunization with DNA encoding fragment C of tetanus toxin, Inf. Immun. 64(8): 3168–3173.

Kaul et al, "Expression of the *Chlamydia trachomatis* major outer membrane protein–encoding gene in *Escherichia coli*: role of the 3' end in mRNA stability," Gene 87(1):97–104.

Douglas et al, "Mutagenesis of the P2 promoter of the major outer membrane protein gene of *Chlamydia trachomatis*", J. Bacteriol., 178(19):5573–5578.

Dascher et al, "Expression and translocation of the chlamydial major outer membrane protein in *Escherichia coli*", Microbial Pathogenesis, 15: 455–467.

* cited by examiner

* p<0.05, **p<0.01, when compared with pcDNA3 group

FIG.3A

*Chlamydia trachomatis* Serine threonine kinase gene (STK)

>stk gene, 1467 bases

```
1      ATG CTT GAA TTA GGC GTA TCG TTT CCT TCC AAG ACT AAA TAT CTT   45
46     CTG ACA CGA GAA CTT AGT CGT AAG GTA GGC TTG ACT GTC TAT CAA   90
91     GGA GTG GAT GAG AGT TCT TCT CGT CCT GTG GTG ATC AAA GCA TTG   135
136    GTA TCT CCA GGG ATT CAT GAC CAG CGT TTT CTT CGT GCT TTT GAA   180
181    GAA GAA GCT AGG ATT ATG CAA CTT GTA GAT CAT CCG GCA TTT GTT   225
226    CGA TTA GAA GAA AAA GGT GAG TGG GAG CAA GGA CGT TAT TTC GTT   270
271    TCT GAA TAT ATT TTA GGG CAT TCA TTG CGA GAT ATT ATC CTT TCA   315
316    TCT CAT CTC GCT TTG GAT AAG GCA GTT TCT ATT GTT TTA CAA GTA   360
361    GCG CAG GCA ATA ACG GCT CTT CAT AAA CAT CAT GTT TTA CAT CTC   405
406    GAT ATT AAA CCT GAA AAC ATC ATG ATT TCT CGG TTG GGA GAG GTC   450
451    AAG TTG ATC GAT TAT GGG CTT TCA GCC TGG CAA TTT AAT CAT TGG   495
496    GGT TCG CCT GCA TAT ATG AGT CCC GAA CAG AGC AGG CAG GAA AAG   540
541    CTA TCT CCC GCA TCC GAT GTG TAT GCT TTA GCT TTG TTA GCT TAT   585
586    GAG CTG ATT ATG GGG CAG CTT TCT TTA GGA AAG GTC TAT TTA TCT   630
631    TTA CTC CCC GTA AAG ATT AGT AAA GTG TTA ACT CAA GCA TTG CAA   675
676    CCA GAC CCA GAA GCA CGG TTT CCT TCT ATG CAA GAG TTT GCT ACG   720
721    GCT TTG CAA GAT TAT CTT ATG CAT GAT GTG CAC GAA GAT TAT CGT   765
766    AAA AAA GAT CGC GTA ATC ATG CAG TTT GAA CAG TTG CAG CAA CAA   810
811    AAT ATG TGG CTG GCT CCA GAT AAG CTT TGC ATG CCG GAA GGG ATG   855
856    GCT CTG CAC ATT TAT TCA CAA AAA GAG CCC TGT GAT TTA CAT AAT   900
901    GTT TAC TAT GAT ATA CTT AGG TCT GAG GAT ATA GTA GAA TTG TGG   945
```

FIG.3B

```
946   TTC TGT TAT GCT CAG GGG CAC TGT CTT AGT ATG ATC   990
991   AAA CAG TTT CTT AAT CAG AAA GCG CAA GCG ATC CCA  1035
1036  ACA GTA ATA AAA ACA CGA ACA CTT TGT AAA ACA CAT ATT  1080
1081  CCG CTT TGT GAA AAA TTG GAT ACT TCC TGC ATT TTT TTC  1125
1126  CAA CAA GAA CTC ATG TGC TTT TCT TGT GGG AAA ACT GAT TTC TCG  1170
1171  TTA AAA CAA ACG AGG GGA CGT CAA GTG GCG GAA TCG  1215
1216  CAA GGA ATA GGG GAG CCC CTG ATC CAC AAA CAA TCT  1260
1261  TTT TTG TGG GAA CCT GGT GAG CTT ATC GTA CAC ACC CCG AGG  1305
1306  GCT AGA GAT TTG GTA TAT TGT CCT TCT TTC CTG AAG TTG  1350
1351  CAA GAT AGA GGG CAA ATG GAT TTC TGC CAA ACA GAT CTT  1395
1396  CAG AAG GAA GTG AGG CAG TAT GAC GGA AGT TAC CCT  1440
1441  ACA CTT ATC AGC TTA AAA AGA GTC CGG TCA  1467
```

DNA IMMUNIZATION AGAINST CHLAMYDIA INFECTION

FIELD OF INVENTION

The present invention relates to immunology and, in particular, to immunization of hosts using nucleic acid to provide protection against infection by Chlamydia.

BACKGROUND OF INVENTION

DNA immunization is an approach for generating protective immunity against infectious diseases (ref. 1 throughout this application, various references are cited in parentheses to describe more fully the state of the art to which this invention pertains. Full bibliographic information for each citation is found at the end of the specification, immediately preceding the claims. The disclosure of these references are hereby incorporated by reference into the present disclosure). Unlike protein or peptide based subunit vaccines, DNA immunization provides protective immunity through expression of foreign proteins by host cells, thus allowing the presentation of antigen to the immune system in a manner more analogous to that which occurs during infection with viruses or intracellular pathogens (ref. 2). Although considerable interest has been generated by this technique, successful immunity has been most consistently induced by DNA immunization for viral diseases (ref. 3). Results have been more variable with non-viral pathogens which may reflect differences in the nature of the pathogens, in the immunizing antigens chosen, and in the routes of immunization (ref. 4). Further development of DNA vaccination will depend on elucidating the underlying immunological mechanisms and broadening its application to other infectious diseases for which existing strategies of vaccine development have failed.

*Chlamydia trachomatis* is an obligate intracellular bacterial pathogen which usually remains localized to mucosal epithelial surfaces of the human host. Chlamydiae are dimorphic bacteria with an extracellular spore-like transmission cell termed the elementary body (EB) and an intracellular replicative cell termed the reticulate body (ref. 5). From a public health perspective, chlamydial infections are of great importance because they are significant causes of infertility, blindness and are a prevalent co-factor facilitating the transmission of human immunodeficiency virus type 1 (ref. 6). Protective immunity to *C. trachomatis* is effected through cytokines released by Thl-like CD 4 lymphocyte responses and by local antibody in mucosal secretions and is believed to be primarily directed to the major outer membrane protein (MOMP), which is quantitatively the dominant surface protein on the chlamydial bacterial cell and has a molecular mass of about 40 kDa (ret. 16).

Initial efforts in developing a chlamydial vaccine were based on parenteral immunization with the whole bacterial cell. Although this approach met with success in human trials, it was limited because protection was short-lived, partial and vaccination may exacerbate disease during subsequent infection episodes possibly due to pathological reactions to certain chlamydial antigens (ref. 8). More recent attempts at chlamydial vaccine design have been based on a subunit design using MOMP protein or peptides. These subunit vaccines have also generally failed, perhaps because the immunogens do not induce protective cellular and humoral immune responses recalled by native epitopes on the organism (ref. 9).

In copending U.S. patent application Ser. No. 08/893,381 filed Jul. 11, 1997, (U.S. Pat. No. 6,235,290) assigned to University of Manitoba and the disclosure of which is incorporated herein by reference (WO 98/02546), I have described the generation of a protective immune response using a DNA sequence which encodes the MOMP of *C. trachomatis* in a plasmid by DNA immunization.

SUMMARY OF THE INVENTION

The present invention is concerned with nucleic acid immunization, specifically DNA immunization, to generate in a host protective antibodies to a serine-threonine kinase of a strain of Chlamydia. DNA immunization induces a broad spectrum of immune responses including Thl-like CD4 responses and mucosal immunity.

Accordingly, in one aspect, the present invention provides a non-replicating vector comprising a nucleotide sequence encoding a serine-threonine kinase (STK) or a fragment of STK that generates a STK-specific immune response, and a promoter sequence operatively coupled to said nucleotide sequence for expression of said STK in a host to which the vector is administered.

The promoter may be a cytomegalovirus promoter, and may be contained in the human cytomegalovirus major immediate-early promoter-enhancer region. The vector may be a plasmid vector and the nucleotide sequence may be those of SEQ ID No: 1.

The strain of Chlamydia may be a strain of Chlamydia inducing chlamydial infection of the lung, including *Chlamydia trachomatis* or *Chlamydia pneumoniae*. The non-replicating vector may be plasmid pcDNA3 into which the nucleotide sequence is inserted. The pcDNA3 vector may contain the nucleotide sequence having SEQ ID No: 1.

In a further aspect of the present invention there is provided an immunogenic composition for in vivo administration to a host for the generation in the host of a protective immune response to a serine-threonine kinase (STK) of a strain of Chlamydia, comprising a non-replicating vector as provided herein and a pharmaceutically-acceptable carrier therefor.

In an additional aspect of the invention, there is provided as a method of immunizing a host against disease caused by infection with a strain of Chlamydia, which comprises administering to said host an effective amount of a non-replicating vector as provided herein.

In these aspects of the present invention, the various options and alternatives discussed above for the non-replicating vector may be employed.

The non-replicating vector may be administrated to the host, including a human host, in any convenient manner, such as intramuscularly or intranasally.

The present invention also includes, in a further aspect thereof, a method of using a gene encoding a serine-threonine kinase (STK) of a strain of Chlamydia or a fragment of said STK that generates a STK-specific immune response, to produce an immune response in a host, which comprises isolating said gene; operatively linking said gene to at least one control sequence to, produce a non-replicating vector, said control sequence directing expression of said STK when introduced into a host to produce an immune response to said STK; and introducing said vector into a host.

In an additional aspect of the invention, there is provided a method of producing a vaccine for protection of a host against disease caused by infection with a strain of Chlamydia, which comprises isolating a nucleotide sequence encoding a serine-threonine kinase (STK) of a strain of Chlamydia or a fragment of the STK that generates a STK-specific immune response, operatively linking said nucleotide sequence to at least one control sequence to produce a non-replicating vector, the control sequence directing expression of said STK when introduced co a host to produce an immune response to said STK, and formulating said vector as a vaccine for in vivo administration to a host.

The various options and alternatives discussed above may be employed in this aspect of the invention.

Advantages of the present invention, therefore, include a method of obtaining a protective immune response to infection carried by a strain of Chlamydia by DNA immunization of DNA encoding the major outer membrane protein of a strain of Chlamydia.

BRIEF DESCRIPTION OF DRAWINGS

FIG. 1A shows body weight of the mice was measured daily after challenge infection until mice were sacrificed at day 10. FIG. 1B shows mice were sacrificed at postinfection day 10, and MoPn growth in lung was analyzed by quantitative tissue culture. Data are mean ±SE of $\log_{10}$ IFU/lung. *$p<0.05$, $p<0.01$ vs. pcDNA-treated group. EB=host-killed elementary bodies, STK=plasmid DNA, Nonative, pcDNA3=empty vector.

FIGS. 3A and 3B show the nucleic acid sequence of the STK gene (SEQ ID No: 1).

GENERAL DESCRIPTION OF THE INVENTION

Figure 1A:
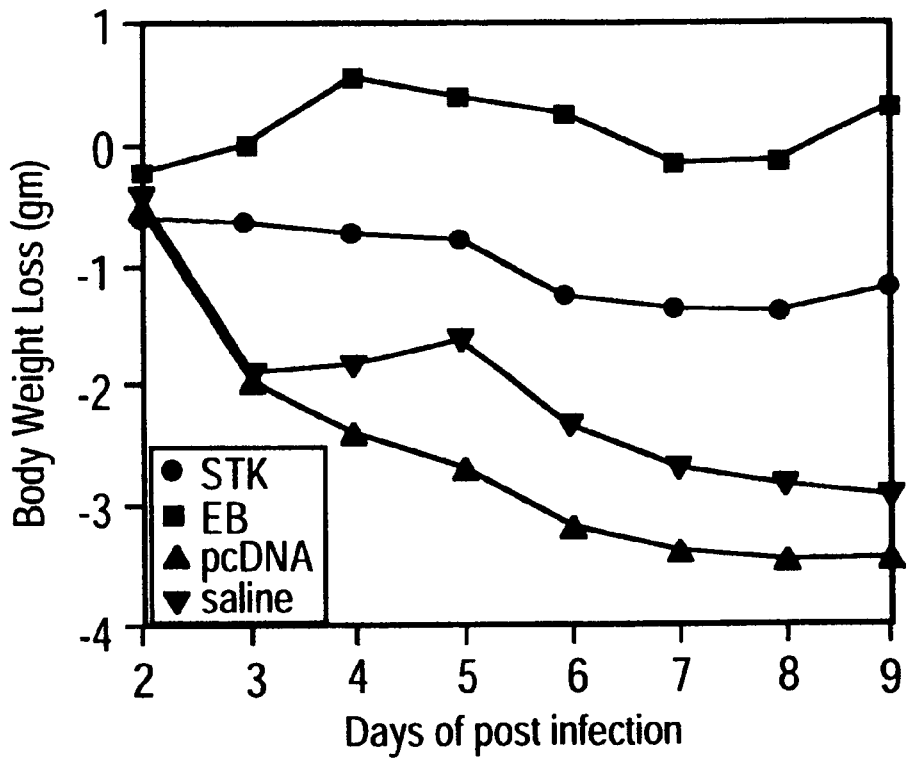
FIG. 1A and FIG. 1B show the results of immunization with serine-threonine kinase gene (pSTK)-enhanced clearance of mouse pneumonitis (MoPn) infection in lung. Groups Balb/c mice were immunized with pSTK (n=5), pcDNA3 (n=6), saline (n=5) or with 1000 IFU of live MoPn EB (n=6). Fourteen days after last immunization, mice were challenged intranasally with infectious MoPn (2000 IFU).
Figure 1B:
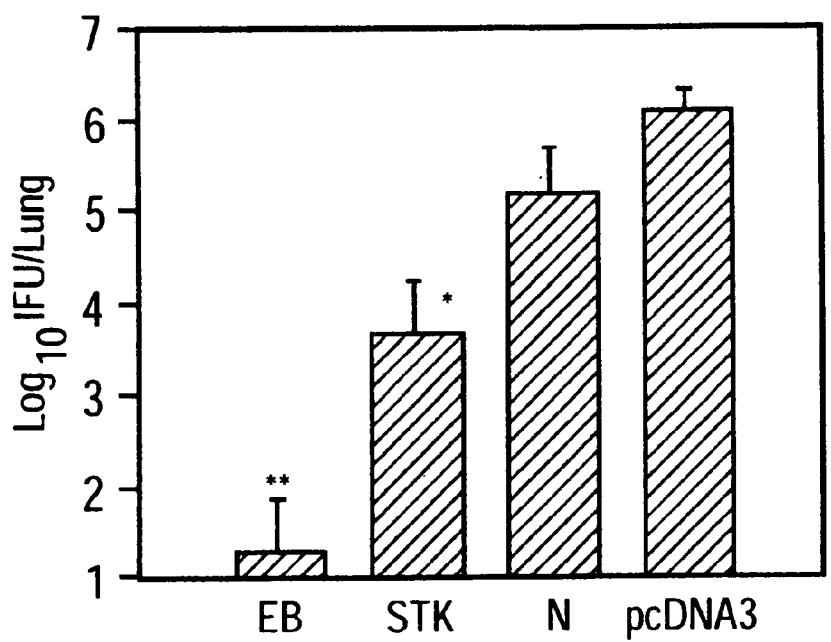
Figure 2:
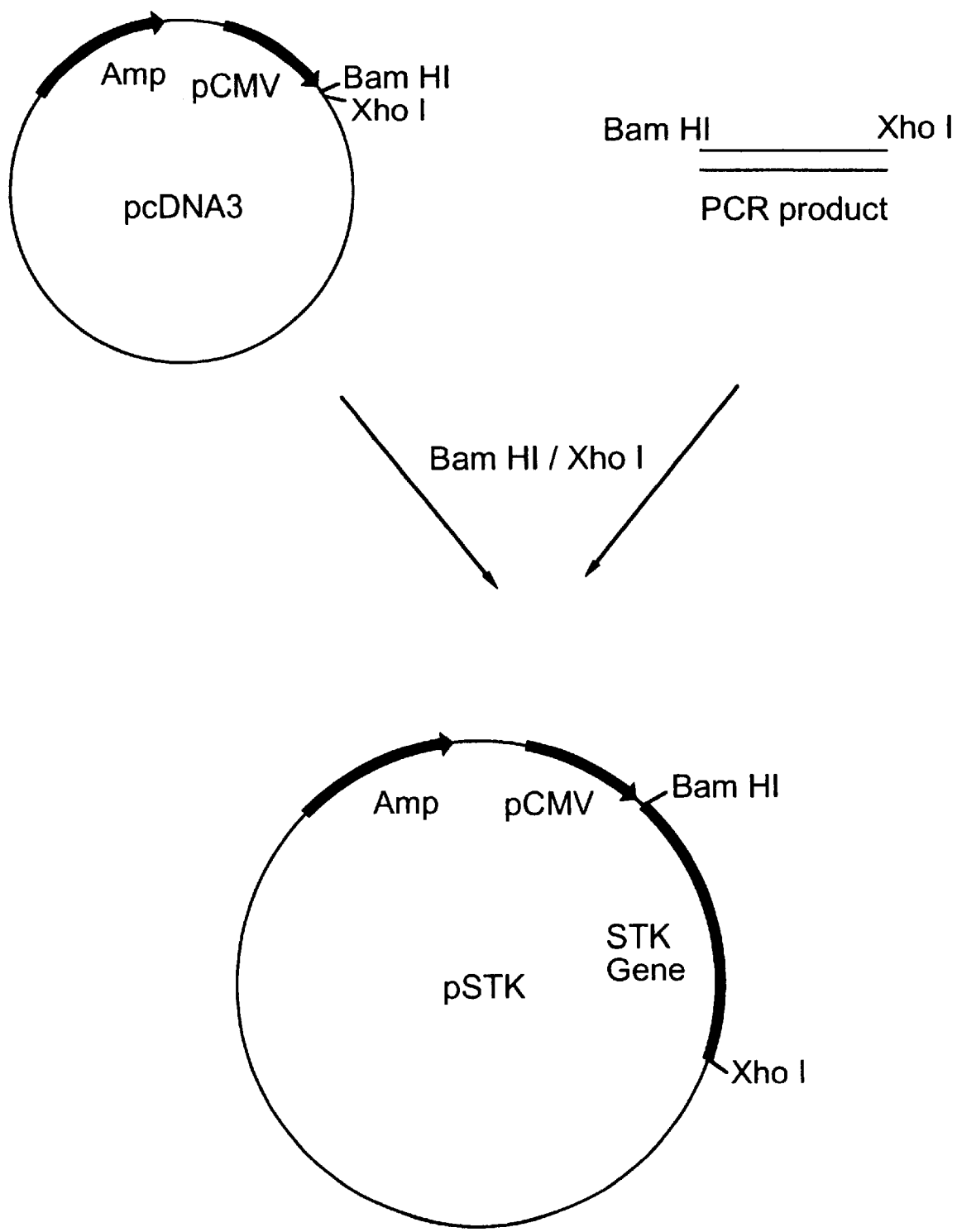
FIG. 2 shows the construction of plasmid pcDNA3/STK.

To illustrate the present invention, plasmid DNA was constructed containing the serine-threonine kinase (STK) gene from the *C. trachomatis* mouse pneumonitis strain (MoPn), which is a natural murine pathogen, permitting experimentation to be effected in mice. It is known that primary infection in the mouse model induces strong protective immunity to reinfection. For human immunization, a human pathogen strain is used.

Any convenient plasmid vector may be used, such as pcDNA3, a eukaryotic II-selectable expression vector (Invitrogen, San Diego, Calif., USA), containing a human cytomegalovirus major-immediate-early promoter-enhancer region. The STK gene may be inserted in the vector in any convenient manner. The gene may be amplified from *Chlamydia trachomatic* genomic DNA by PCR using suitable primers and the PCR product cloned into the vector. The STK gene-carrying plasmid may be transferred, such as by electroporation, into *E. coli* for replication therein. Plasmids may be extracted from the *E. coli* in any convenient manner.

The plasmid containing the STK gene may be administered in any convenient manner to the host, such as intramuscularly or intranasally, in conjunction with a pharmaceutically-acceptable carrier.

The data presented herein and described in detail below demonstrates that DNA immunization with the *C. trachomatis* STK gene elicits immune responses and produces significant protective immunity to lung challenge infection with *C. trachomatis* MoPn.

It is clearly apparent to one skilled in the art, that the various embodiments of the present invention have many applications in the fields of vaccination, diagnosis and treatment of chlamydial infections. A further non-limiting discussion of such uses is further presented below.

1. Vaccine Preparation and Use

Immunogenic compositions, suitable to be used as vaccines, may be prepared from the STK genes and vectors as disclosed herein. The vaccine elicits an immune response in a subject which includes the production of anti-STK antibodies. Immunogenic compositions, including vaccines, containing the nucleic acid may be prepared as injectables, in physiologically-acceptable liquid solutions or emulsions for polynucleotide administration. The nucleic acid may be associated with liposomes, such as lecithin liposomes or other liposomes known in the art, as a nucleic acid liposome (for example, as described in WO 9324640) or the nucleic acid may be associated with an adjuvant, as described in more detail below. Liposomes comprising cationic lipids interact spontaneously and rapidly with polyanions, such as DNA and RNA, resulting in liposome/nucleic acid complexes that capture up to 100% of the polynucleotide. In addition, the polycationic complexes fuse with cell membranes, resulting in an intracellular delivery of polynucleotide that bypasses the degradative enzymes of the lysosomal compartment. Published PCT application WO 94/27435 describes compositions for genetic immunization comprising cationic lipids and polynucleotides. Agents which assist in the cellular uptake of nucleic acid, such as calcium ions, viral proteins and other transfection facilitating agents, may advantageously be used.

Polynucleotide immunogenic preparations may also be formulated as microcapsules, including biodegradable time-release particles. Thus, U.S. Pat. No. 5,151,264 describes a particulate carrier of a phospholipid/glycolipid/polysaccharide nature that has been termed Bio Vecteurs Supra Moleculaires (BVSM). The particulate carriers are intended to transport a variety of molecules having biological activity in one of the layers thereof.

U.S. Pat. No. 5,075,109 describes encapsulation of the antigens trinitrophenylated keyhole limpet hemocyanin and staphylococcal enterotoxin B in 50;50 poly (DL-lactideco-glycolide). Other polymers for encapsulation are suggested, such as poly(glycolide), poly(DL-lactide-co-glycolide), copolyoxalates, polycaprolactone, poly(lactide-co-caprolactone), poly(esteramides), polyorthoesters and poly (8-hydroxybutyric acid), and polyanhydrides.

Published PCT application WO 91/06282 describes a delivery vehicle comprising a plurality of bioadhesive microspheres and antigens. The microspheres being of starch, gelatin, dextran, collagen or albumin. This delivery vehicle 1 s particularly intended for the uptake of vaccine across the nasal mucosa. The delivery vehicle may additionally contain an absorption enhancer.

The STK gene containing non-replicating vectors may be mixed with pharmaceutically acceptable excipients which are compatible therewith. Such excipients may include, water, saline, dextrose, glycerol, ethanol, and combinations thereof. The immunogenic compositions and vaccines may further contain auxiliary substances, such as wetting or emulsifying agents, pH buffering agents, or adjuvants to enhance the effectiveness thereof. Immunogenic compositions and vaccines may be administered parenterally, by injection subcutaneously, intravenously, intradermally or intramuscularly, possibly following pretreatment of the injection size with a local anesthetic. Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. Alternatively, other modes of administration including suppositories and oral formulations may be desirable. For suppositories, binders and carriers may include, for example, polyalkylene glycols or triglycerides. Oral formulations may include normally employed incipients, such as, for example, pharmaceutical grades of saccharine, cellulose and magnesium carbonate.

The immunogenic preparations and vaccines are administered in a manner compatible with the dosage formulation, and in such amount as will be therapeutically effective, protective and immunogenic. The quantity to be administered depends on the subject to be treated, including, for example, the capacity of the individual's immune system to synthesize the STK and antibodies thereto, and if needed, to produce a cell-mediated immune response. Precise amounts of active ingredient required to be administered depend on the judgement of the practitioner. However, suitable dosage ranges are readily determinable by one skilled in the art and may be of the order of about 1 $\mu$g to about 1 mg of the STK gene-containing vectors. Suitable regimes for initial administration and booster doses are also variable, but may include an initial administration followed by subsequent administrations. The dosage may also depend on the route of administration and will vary according to the size of the host. A vaccine which protects against only one pathogen is a monovalent vaccine. Vaccines which contain antigenic material of several pathogens are combined vaccines and also belong to the present invention. Such combined vaccines contain, for example, material from various pathogens or from various strains of the same pathogen, or from combinations of various pathogens.

Immunogenicity can be significantly improved if the vectors are co-administered with adjuvants, commonly used as 0.05 to 0.1 percent solution in phosphate-buffered saline. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Thus, adjuvants have been identified that enhance the immune response to antigens. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines.

A wide range of extrinsic adjuvants and other immunomodulating material can provoke potent immune responses to antigens. These include saponins completed to membrane protein antigens to produce immune stimulating complexes (ISCOMS), pluronic polymers with mineral oil, killed mycobacteria in mineral oil, Freund's complete adjuvant, bacterial products, such as muramyl dipeptide (MDP) and lipopolysaccharide (LPS), as well as monophoryl lipid A, QS 21 and polyphosphazene.

In particular embodiments of the present invention, the non-replicating vector comprising a first nucleotide sequence encoding a STK gene of Chlamydia may be delivered in conjunction with a targeting molecule to target the vector to selected cells including cells of the immune system.

The non-replicating vector may be delivered to the host by a variety of procedures, for example, Tang et al. (ref. 14) disclosed that introduction of gold microprojectiles coated with DNA encoding bovine growth hormone (BGH) into the skin of mice resulted in production of anti-BGH antibodies in the mice, while Furth et al. (ref. 15) showed that a jet injector could be used to transfect skin, muscle, fat and mammary tissues of living animals.

2. Immunoassays

The STK genes and vectors of the present invention are useful as immunogens for the generation of anti-STK antibodies for use in immunoassays, including enzyme-linked immunosorbent assays (ELISA), RIAs and other non-enzyme linked antibody binding assays or procedures known in the art. In ELISA assays, the non-replicating vector first is administered to a host to generate antibodies specific to the STK. These STK specific antibodies are immobilized onto a selected surface, for example, a surface capable of binding the antibodies, such as the wells of a polystyrene microliter plate. After washing to remove incompletely adsorbed antibodies, a nonspecific protein, such as a solution of bovine serum albumin (BSA) that is known to be antigenically neutral with regard to the test sample, may be bound to the selected surface. This allows for blocking of nonspecific adsorption sites on the immobilizing surface and thus reduces the background caused by nonspecific bindings of antisera onto the surface.

The immobilizing surface is then contacted with a sample, such as clinical or biological materials, to be tested in a manner conducive to immune complex (antigen/antibody) formation. This procedure may include diluting the sample with diluents, such as solutions of BSA, bovine gamma globulin (BGG) and/or phosphate buffered saline (PBS)/Tween. The sample is then allowed to incubate for from about 2 to 4 hours, at temperatures such as of the order of about 20° to 37° C. Following incubation, the sample-contacted surface is washed to remove non-immunocomplexed material. The washing procedure may include washing with a solution, such as PBS/Tween or a borate buffer. Following formation of specific immunocomplexes between the rest sample and the bound STK specific antibodies, and subsequent washing, the occurrence, and even amount, of immunocomplex formation may be determined.

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

Example 1

This Example shows the preparation of a plasmid vector for immunization.

The *C. trachomatis* mouse pneumonitis (MoPn) isolate was grown in HeLa 229 cells in Eagle MEM containing 10% fetal bovine serum and 2 mM L-glutamine. The MoPn EBs were harvested and purified by step gradient density centrifugation at 43,000 g for 60 min at 4° C. The purified EBs were washed twice with PBS, centifugated at 30,000 g for 30 min, resuspended in sucrose-phosphate-glutamic acid (SPG) buffer and frozen at −70° C. until used.

The serine-threonine kinase (STK) gene was cloned into eukaryotic expression plasmid, pcDNA3 (Invitrogen, San Diego) to form plasmid pcDNA3/STK. The STK gene was amplified from MoPn genomic DNA by polymerase chain reaction (PCR) with a 5' primer (GGG GAT CCG CCA CCA TGC TTG AAT TAG GCG TAT CGT TTC CT—SEQ ID No: 2) which included a BamHI site, a start cod6 n, and the N-terminal sequence of the mature serine-threonine kinase of MoPn and a 3' primer (GGG GCT CGA GCT ATT ACC GGA CTC TTT TTA AGC TGA TAA G—SEQ ID No: 3) which include a XhoI site, two stop codons (CTA TTA), and the C-terminal sequence of the MoPn STK gene. After digestion with BamHI and XhoI, the PCR product, having the sequence shown in FIGS. 3A and 3B (SEQ ID No: 1), was cloned into BamHI and XhoI restricted pcDNA3 with transcription under the control of human cytomegalovirus major intermediate-early promoter-enhancer region. The STK gene-encoding plasmid was transferred by electroporation into *Escherichia Coli* DH5$_\alpha$, which was grown in luria-Bertani broth containing 100 μg/ml ampicillin. The plasmid was extracted by a DNA purification system (Wizard Plus Maxiprep; promega, Madison, Wis.), and the sequence of recombinant STK DNA was verified by PCR direct sequence analysis. Purified plasmid DNA was dissolved in saline at a concentration of 1 mg/ml. The DNA concentration was determined by spectrophotometry (DU-62; Backman, Fullerton, Calif.) at 260 nm, and the size of the plasmid-was compared with DNA standards in a ethidium bromide-stained agarose gel.

Example 2

This Example shows the results of immunizing studies using the plasmid vector.

Female Balb/c mice (4 to 5 weeks old) were purchased from Charles River Canada (Sr. Constant, Canada) mice were intramuscularly and intranasally immunized with plasmid DNA, prepared as described in Example 1, on three occasions, at 0, 2 and 4 weeks. For each immunization, a total of 200 μg DNA in 200 μl was injected into the two quadriceps muscles (100 μg of DNA/injection site) using a 27-gauge needle. At the same season, 50 μg DNA in 50 μl was delivered onto the nostrils of mice with a micropipette. The droplet was subsequently inhaled by the mice.

Mice were challenged intranasally with $2 \times 10^3$ IFU of *C. trachomatis MoPn ED* 14 days after last immunization, as described. Briefly, after ether anesthesia 25 μl of SPG containing an inoculum of $2 \times 10^3$ IFU of MoPn was delivered onto the nostrils of mice with a micropipette. The droplet was subsequently inhalted by the mice. Body weight was measured daily for 10 days following the challenge infection as a measure of chlamydia-induced morbidity. On postinfection day 10, the mice were sacrificed and their lungs were aseptically isolated and homogenized with grinder in SPG buffer. The tissue suspensions were centrifuged at 500 g for 10 min at 4° C. remove coarse tissue and debris. Supernatants were frozen at −70° C. until tissue culture testing for quantitative growth of the organism.

For more direct measure of the effectiveness of the DNA vaccination, the ability to limit the in vivo growth of Chlamydia following a sublethal lung infection was evaluated. In this infection model system, postchallenge day 10 is the time of peak growth and was chosen for comparison of lung titers among the various groups of mice. Mice immunized with STK DNA had a lung titer ($\log_{10}$ IFU) is 31.6 and 316.2 folds lower than negative control groups (blank vector and saline groups).

SUMMARY OF DISCLOSURE

In summary of this disclosure, the present invention provides a method of nucleic acid, including DNA, immunization of a host, including humans, against disease caused by infection by strain of Chlamydia, specifically *C. trachomatis*, employing a non-replicating vector, specifically a plasmid vector, containing a nucleotide sequence encoding a serine-threonine kinase (STK) of a strain of Chlamydia and a promoter to effect expression of STK in the host. Modifications are possible within the scope of this invention.

REFERENCES

1. M. A. Liu, M. R. Hilleman, R. Kurch, Ann. N.Y. Acad. Sci. 772 (1995).
2. D. M. Pardoll and A. M. Beckerieg, Immunity 3, 165 (1995); W. M. McDonnell and F. K. Askari, N. Engl. J. Med. 334, 42 (1996).
3. J. B. Ulmer et al., Science 259, 1745 (1993); B. Wang et al., Proc. Natl. Acad. Sci. USA 90, 4156 (1993); G. J. M. Cox, T. J. Zamb, L. A. Babiuk, J. Virol. 67, 5664 (1993); E. Raz et al., Proc. Natl. Acad. Sci. USA, 91,9519 (1994); Z. Q. Xiang et al., Virology 199, 132 (1994); J. J. Donnelly et al., J. Infect. Dis. 713, 314 (1996); D. L. Montgomery et al., DNA. Cell. Biol. 12, 777 (1993); J. J. Donnelly et al., Nature Medicine 1, 583 (1995); G. H. Rhodes et al., Dev. Biol. Stand. 82, 229 (1994); H. L. Davis, M. L. Michel, R. G. Whalen, Human Molecular Genetics 2, 1847 (1993);. J. B. Ulmer et al., Vaccine 12, 1541 (1994); Z. Xiang and H. C. J. Ertl. Immunity 2. 129 (1995); E. F. Fynan et al, Proc. Natl. Acad. Sci. USA 90, 11478 (1993); E. Manickan, R. J. D. Rouse, Z. Yu, J. Immunol. 155, 259 (1995).
4. M. Sedegah, R. Hedstrom, P. Hobart, S. L., Hoffman, Proc. Natl. Acad. Sci. USA 91, 9866 (1994); M. A. Barry, W. C. Lai, S. A. Johnston, Nature 377, 632 (1995); D. Xu and F. Y. Liew, Vaccine 12, 1534 (1994); D. B. Lowrie, R. E. Tascon, M. J. Colston, vaccine 12, 1537 (1994).
5. J. W. Moulder, Microbiol. Rev. 55, 143 (1991).
6. J. Schachter, Curr. Top. Microbiol. Immunol. 138, 109 (1988); S. D. Hillis and J. N. Wasserheit, N. Engl. J. Med. 334, 1399 (1996).
7. R. C. Brunham and R. W. Peeling, Infectious Agents and Disease 3, 218 (1994);. R. P. Morrison, D. S. Manning, H. D. Caldwell, in Advances in Host Defence Mechanisms, T. C. Quin, Ed. (Raven Press, New. York, 1992), pp 17–84.
8. J. T. Grayston and S.-P. Wang, Sex. Trans. Dis. 5, 73 (1978); J. T. Grayston and S.-P. Wang, J. Infect. Dis. 132, 87 (1975).
9. H. R. Taylor, J. Whittum-Hudson, J. Schachter, Invest. Ophthalmol. Vis. Sci. 29, 1847 (1988); B. E. Batteiger, R. G. Rank, P. M. Bavoil, J. Gen. Microbiol. 139, 2965 (1993); M. Campos et al., Invest. Ophthalmol. Vis. Sci. 36, 1477 (1995); H. Su, M. Parnell, H. D. Caldwell, Vaccine 13, 1023 (1995); T.-W. Tan, A. J. Herring, I. E. Anderson, Infect. Immun. 58, 3101 (1990);: M. Tuffrey, F. Alexander, W. Conlan, J. Gen. Microbiol. 138, 1707 (1992).
10. Y.-X. Zhang, J. G. Fox, Y. Ho, Mol. Biol. Evol. 10, 1327 (1993).
11. R. P. Morrison, K. Feilzer, D. B. Tumas, Infect. Immun. 63, 4661 (1995); H. Su and H. D. Caldwell, Infect. Immun. 63, 3302 (1995); J. U. Igietseme et al., Reg. Immunol. 5, 317 (1993); J. U. Igietseme and R. G. Rank, Infect. Immun. 59, 1346 (1991); D. M. Williams, J. Schachter, J. J. Coalson, J. Infect. Dis. 149, 630 (1984).
12. G. Tipples and G. McClarty, J. Biol. Chem. 270, 7908 (1995).
13. X. Yang, K. T. HayGlass, R. C. Brunham, J. Immunol., 156, 4338 (1996).
14. Tang et al., Nature 1992, 356: 152–154.
15. Furth et al., Vaccine 1994, 12: 1503–1509.
16. Morrison R P, Manning D S, Caldwell H D. Immunology of *Chlamydia trachomatis* infections: Immunoprotective and immunopathogenetic responses. In: Quin T C. Advances in host defence mechanisms. Sexually transmitted diseases. vol. 8. New York: Raven Press, 1992: 52–84.

What I claim is:

1. A pcDNA3 plasmid vector comprising:

a nucleotide sequence encoding a serine-threonine kinase (STK) of a strain of *Chlamydia trachomatis*, and consisting of SEQ ID No: 1, and a promoter sequence operatively coupled to said nucleotide sequence for expression of said STK in a host to which the vector is administered, said promoter sequence being the human cytomegalovirus major intermediate-early promoter-enhancer region.

* * * * *

SEQUENCE LISTING

<160> NUMBER OF SEQ ID NOS: 3

<210> SEQ ID NO 1
<211> LENGTH: 1467
<212> TYPE: DNA
<213> ORGANISM: Chlamydia trachomatis

<400> SEQUENCE: 1

```
atgcttgaat taggcgtatc gtttccttcc aagactaaat atcttctgac acgagaactt      60
agtcgtaagg taggcttgac tgtctatcaa ggagtggatg agagttcttc tcgtcctgtg     120
gtgatcaaag cattggtatc tccagggatt catgaccagc gtttcttcg tgcttttgaa      180 gaagaagcta ggattatgca acttgtagat catccggcat ttgttcgatt agaagaaaaa     240
ggtgagtggg agcaaggacg ttatttcgtt tctgaatata ttttagggca ttcattgcga     300
gatattatcc tttcatctca tctcgctttg gataaggcag tttctattgt tttacaagta     360
gcgcaggcaa taacggctct tcataaacat catgttttac atctcgatat taaacctgaa     420
aacatcatga tttctcggtt gggagaggtc aagttgatcg attatgggct ttcagcctgg     480
caatttaatc attggggttc gcctgcatat atgagtcccg aacagagcag gcaggaaaag     540
ctatctcccg catccgatgt gtatgcttta gctttgttag cttatgagct gattatgggg     600
cagctttctt taggaaaggt ctatttatct ttactccccg taaagattag taaagtgtta     660
actcaagcat tgcaaccaga cccagaagca cggtttcctt ctatgcaaga gtttgctacg     720
```

-continued

```
gctttgcaag attatcttat gcatgatgtg cacgaagatt atcgtaaaaa agatcgcgta      780
atcatgcagt ttgaacagtt gcagcaacaa aatatgtggc tggctccaga taagctttgc      840
atgccggaag ggatggctct gcacatttat tcacaaaaag agccctgtga tttacataat      900
gtttactatg atatacttag gtctgaggat atagtagaat tgtggttctg ttatgctcag      960
gggcactgta gttttgctct tagtatgatc aaacagtttc ttaatcagcg aacagagaaa     1020
gcgcaagata tcccaacagt aataaaaaca ttggatactc tttgtaaaac aatgcatatt     1080
ccgctttgtg aaaagggat ttcctgctgc tgttttatat ttttccaaca agaactcatg      1140 tgctttctt gtgggaaaac tgatttctcg ttaaaaaagc aaacgagggg agtgcaacgt      1200
tttcaagcgg aatcgcaagg aatagggaa gagggacccc tggagatcca caaacaatct      1260
tttttgtggg aacctggtga tgagcttatc gtacacaccc cgagggctag agatttggta     1320
tatttatact gtccttcttt cctgaagttg caagatagag ggcaaatgga tatattctgc     1380
caaacagatt accttcagaa ggaagtgagg cagaagtatg acggaagtct ttatccttca     1440
acacttatca gcttaaaaag agtccgg                                         1467
```

<210> SEQ ID NO 2
<211> LENGTH: 41
<212> TYPE: DNA
<213> ORGANISM: Chlamydia trachomatis

<400> SEQUENCE: 2

```
ggggatccgc caccatgctt gaattaggcg tatcgtttcc t                           41
```

<210> SEQ ID NO 3
<211> LENGTH: 40
<212> TYPE: DNA
<213> ORGANISM: Chlamydia trachomatis

<400> SEQUENCE: 3

```
ggggctcgag ctattaccgg actcttttta agctgataag                             40
```